(12) United States Patent
Ii et al.

(10) Patent No.: US 8,304,585 B2
(45) Date of Patent: Nov. 6, 2012

(54) PRODUCTION PROCESS OF 1,6-HEXANEDIOL

(75) Inventors: Hirofumi Ii, Ube (JP); Tomoyuki Ito, Ube (JP); Yoshiki Kawamura, Ube (JP); Toshiyuki Matsushita, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 1117 days.

(21) Appl. No.: 12/087,422

(22) PCT Filed: Jan. 12, 2007

(86) PCT No.: PCT/JP2007/050286
§ 371 (c)(1),
(2), (4) Date: Jul. 3, 2008

(87) PCT Pub. No.: WO2007/080946
PCT Pub. Date: Jul. 19, 2007

(65) Prior Publication Data
US 2009/0048471 A1 Feb. 19, 2009

(30) Foreign Application Priority Data
Jan. 13, 2006 (JP) .................................. 2006-005802

(51) Int. Cl.
C07C 27/04 (2006.01)
C07C 27/00 (2006.01)
C07C 27/26 (2006.01)
C07C 69/74 (2006.01)

(52) U.S. Cl. ........ 568/884; 568/902; 568/903; 568/910; 568/913; 560/127

(58) Field of Classification Search .................. None
See application file for complete search history.

(56) References Cited

U.S. PATENT DOCUMENTS

| 3,268,588 | A | | 8/1966 | Horlenko et al. |
| 3,524,892 | A | | 8/1970 | Horlenko et al. |
| 3,933,930 | A | | 1/1976 | Dougherty et al. |
| 6,008,418 | A | | 12/1999 | Baur et al. |
| 6,136,869 | A | * | 10/2000 | Ekart et al. ................... 521/48.5 |
| 6,288,286 | B1 | | 9/2001 | Stein et al. |
| 7,307,194 | B2 | * | 12/2007 | Sirch et al. ..................... 568/853 |
| 2007/0112225 | A1 | * | 5/2007 | Sirch et al. ..................... 568/864 |
| 2008/0207958 | A1 | * | 8/2008 | Haunert et al. ................ 568/862 |

FOREIGN PATENT DOCUMENTS

| CA | 2248004 | * | 4/2006 |
| JP | 51-108040 A | | 9/1976 |
| JP | 2000-505468 A | | 5/2000 |
| JP | 2002-516889 A | | 6/2002 |
| WO | WO-97/31882 A1 | | 9/1997 |
| WO | WO 97/31883 A1 | | 9/1997 |
| WO | WO-99/62852 A1 | | 12/1999 |
| WO | WO 2004/026798 A2 | | 4/2004 |

OTHER PUBLICATIONS

Extended European Search Report issued on Nov. 23, 2010 in corresponding European Patent Application No. 07 70 6633.

* cited by examiner

Primary Examiner — Porfirio Nazario Gonzalez
Assistant Examiner — James Meadows
(74) Attorney, Agent, or Firm — Birch, Stewart, Kolasch & Birch, LLP

(57) ABSTRACT

A method is provided for producing highly pure 1,6-hexanediol in which the contents of impurities such as 1,4-cyclohexanediol, 1,5-hexanediol, 1,2-cyclohexanediol, 1,7-pentanediol, 1,5-pentanediol and high boiling point components are significantly reduced. The process contains the steps of (1) treating an aqueous extraction concentrate of a reaction mixture obtained by oxidation of cyclohexane with a lower alcohol to esterify monocarboxylic acids and dicarboxylic acids contained in the extract, and simultaneously removing and separating by distillation water, excess lower alcohols and carboxylic acid esters; (2) converting oligomer esters contained in the bottom liquid to carboxylic acid esters by depolymerizing the oligomer esters at a high temperature and high pressure in the presence of a lower alcohol and a catalyst; and (3) hydrogenating the carboxylic acid esters distilled off in step (1) and the carboxylic acid esters obtained in step (2) either respectively or collectively to convert to 1,6-hexanediol.

6 Claims, 4 Drawing Sheets

Reaction conditions: Catalyst (tetrabutoxytitanium) concentration = 500 ppm, methanol weight ratio = 2, residence time = 5 minutes, DMA: dimethyl adipate, MOC: methyl oxycaproate

US 8,304,585 B2

PRODUCTION PROCESS OF 1,6-HEXANEDIOL

TECHNICAL FIELD

The present invention relates to a production process of 1,6-hexanediol.

BACKGROUND ART 1,6-hexanediol is a useful substance used as a raw material of polyester resins, urethane foam, urethane paint and adhesives. For example, it can be used directly as a chain extender when used as the raw material of polyurethanes, or can be used as a soft segment by using in the production of polycarbonate diols and polyester polyoles.

Although cyclohexanone and/or cyclohexanol, which are useful as raw materials in the synthesis of ε-caprolactam, are produced industrially by aerobic oxidation of cyclohexane, 1,6-hexandiol is produced by esterifying a mixture of carboxylic acids, including glutaric acid, adipic acid, 6-hydroxycaproic acid and so on produced as by-products during aerobic oxidation of cyclohexane, with alcohol followed by hydrogenation to obtain 1,6-hexanediol that is separated by distillation (Patent Documents 1 and 2).

Since the 1,6-hexanediol obtained by the aforementioned method contains impurities such as 1,4-cyclohexanediol, 1,5-hexanediol, 1,2-cyclohexanediol, 1,7-pentanediol, 1,5-pentanediol and high boiling point components, if, for example, a polycarbonate diol is produced using 1,6-hexanediol for the raw material, and this is then used as a raw material to carry out a urethanation reaction, it was found that the polymerization rate is slow, an adequate molecular weight cannot be obtained, and that similar problems occur even in the case of using directly as a chain extender in a urethanation reaction. In addition, there was also the problem of similar effects appearing on the polymerization rate during polyester production as well.

With respect to removal of the impurity, 1,4-cyclohexanediol, Patent Document 3 describes a method for converting the aforementioned mixture of carboxylic acids to cyclohexanone and cyclohexanol by preliminary hydrogenation following esterification of the carboxylic acid mixture with an alcohol, while Patent Document 4 describes a method for obtaining an ester essentially free of 1,4-cyclohexanediol by distillation.

However, the method employing preliminary hydrogenation had the problem of inadequate product purity. In addition, although in the method involving ester distillation it is preferable in that the esters are monomers, in actuality, many of the active ingredients of the carboxylic acid mixture become oligomer esters as a result of concentration following extraction with water, thereby requiring not only esterification of the carboxylic acid monomers but also depolymerization of the oligomer esters in order to obtain 1,6-hexanediol at high yield and high purity. However, in the production processes of the prior art, since esterification of carboxylic acid monomers and depolymerization of oligomer esters are carried out simultaneously, Lewis acid catalysts and basic catalysts effective in depolymerization are deactivated by the water formed by esterification of carboxylic acids and residual carboxylic acids, thereby resulting in the problem of considerable time being required for depolymerization and the problem of corrosion of the reaction vessel by water, carboxylic acids and acid catalysts (such as mineral acids). In addition, although esterification and depolymerization are equilibrium reactions, there was also the problem in being unable to increase the equilibrium reaction yield due to the effects of the water formed. Moreover, considerable equipment was required to separate the esters, water, alcohols and other components formed as a result of esterification.

[Patent Document 1] U.S. Pat. No. 3,524,892
[Patent Document 2] U.S. Pat. No. 3,268,588
[Patent Document 3] Japanese Unexamined Patent Publication No. S51-108040
[Patent Document 4] Japanese Unexamined International Publication No. 2000-505468

DISCLOSURE OF THE INVENTION

Problems to be Solved by the Invention

As a result of conducting extensive studies for the purpose of providing a process for synthesizing 1,6-hexanediol without the aforementioned problems, the inventors of the present invention found that the aforementioned problems are solved by process for producing 1,6-hexanediol from cyclohexane, wherein together with esterifying a carboxylic acid mixture obtained as a by-product of oxidation of cyclohexane, a step in which carboxylic acid esters, water and excess lower alcohols used for esterification are removed from the reaction mixture by distillation is carried out simultaneously, while carrying out a step in which oligomers contained in the bottom liquid are converted to carboxylic acid esters by depolymerization at high temperature and under high pressure in the presence of a catalyst, and that highly pure 1,6-hexanediol can be obtained at high yield in which the contents of impurities such as 1,4-cyclohexanediol, 1,5-hexanediol, 1,2-cyclohexanediol, 1,7-pentanediol, 1,5-pentanediol and high boiling point components have been significantly reduced, thereby leading to completion of the present invention.

Means for Solving the Problems

The present invention relates to a process for producing 1,6-hexanediol from cyclohexane, comprising the steps of:

(1) treating an aqueous extraction concentrate of a reaction mixture obtained by oxidation of cyclohexane with a lower alcohol to esterify monocarboxylic acids and dicarboxylic acids contained in the extract, and simultaneously remove and separate by distillation water, excess lower alcohols and carboxylic acid esters;

(2) converting oligomer esters contained in the bottom liquid to carboxylic acid esters by depolymerizing the oligomer esters at a high temperature and high pressure in the presence of a lower alcohol and a catalyst; and, (3) hydrogenating the carboxylic acid esters distilled off in the step (1) and the carboxylic acid esters obtained in the step (2) either respectively or collectively to convert to 1,6-hexanediol.

EFFECTS OF THE INVENTION

As a result of using the process of the present invention, esterification can be carried out efficiently and with fewer equipment than in the prior art by esterifying while also removing water and organic acids, and in the depolymerization step as well, the reaction rate can be significantly improved without causing deactivation of Lewis acid catalysts and basic catalysts susceptible to the effects of water and acid while also making it possible to inhibit corrosion of the reaction vessel. Moreover, highly pure 1,6-hexanediol can be obtained at good yield in which the contents of impurities that cause a decrease in the polymerization rate during production of polyurethane or polyester, such as 1,4-cyclohexanediol, 1,2-cyclohexanediol and 1,5-hexanediol, are significantly reduced.

BEST MODE FOR CARRYING OUT THE INVENTION

Figure 1:
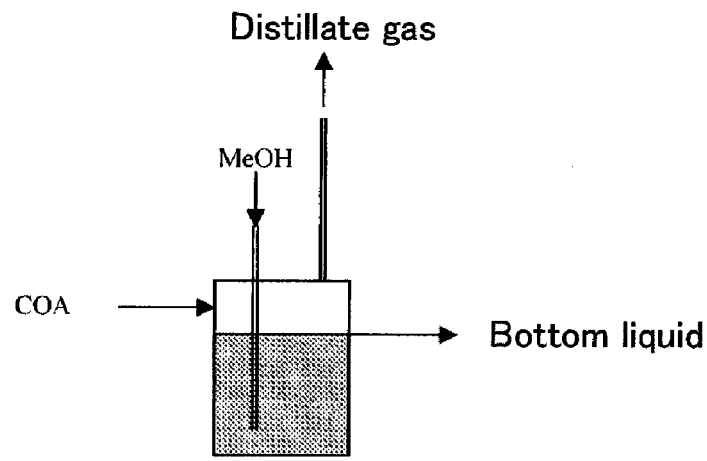
FIG. 1 shows an example of an esterification apparatus of the process of the present invention.

The present invention produces 1,6-hexanediol from cyclohexane by:
(1) carrying out a step in which a reaction mixture obtained by oxidizing cyclohexane with oxygen or an oxygen-containing gas is extracted with water to extract a carboxylic acid mixture containing by-products such as glutaric acid, adipic acid and 6-hydroxycaproic acid, and then the extract is concentrated to have a concentrate which is then treated with a lower alcohol to esterify the monocarboxylic acids and dicarboxylic acids contained in the concentrate, simultaneously with removing and separating by distillation water, excess lower alcohols and carboxylic acid esters;
(2) converting oligomer esters contained in the bottom liquid to carboxylic acid esters such as glutaric acid ester, adipic acid ester or 6-hydroxycaproic acid ester by depolymerizing the oligomer esters at a high temperature and high pressure in the presence of a lower alcohol and a catalyst, and
(3) hydrogenating the carboxylic acid esters distilled off in the step (1) and the carboxylic acid esters obtained in the step (2) either respectively or collectively to convert to 1,6-hexanediol.

The following provides a detailed explanation of the process of the present invention.

In the step (1) of the present invention, a reaction mixture obtained by oxidation of cyclohexane is extracted with water followed by treatment of the concentrated extract with a lower alcohol. As a specific means of obtaining the extract, first the cyclohexane is oxidized with oxygen or an oxygen-containing gas to obtain a mixture containing the main components of cyclohexanone and cyclohexanol and by-products such as glutaric acid, adipic acid and 6-hydroxycaproic acid. Although the method for oxidizing the cyclohexane with oxygen or an oxygen-containing gas can be suitably selected by a person with ordinary skill in the art, an example of such a method is described in Ullmann's Encyclopedia of Industrial Chemistry, 5th edition, 1987, Vol. A8, S.2/9. More specifically, oxygen or an oxygen-containing gas is introduced in a reaction vessel containing cyclohexane followed by using a cobalt or other metal salt (such as cobalt octylate) as a catalyst and carrying out the reaction at a temperature of 150 to 180° C. under a pressure of 0.8 to 1.2 MPa.

Next, by treating the resulting oxidized reaction mixture with water, the carboxylic acid mixture is extracted into an aqueous phase followed by separation from the cyclohexanone and cyclohexanol. During the extraction, extraction can be carried out using for example, 1 to 10% by weight of water with respect to the oxidized reaction mixture.

At this stage, the extracted aqueous phase typically contains 1 to 4% by weight of adipic acid, 1 to 4% by weight of 6-hydroxycaproic acid, 0.01 to 1% by weight of glutaric acid, 0.01 to 1% by weight of 5-hydroxyvaleric acid, 0.01 to 0.5% by weight of 1,2-cyclohexanediol (both cis and trans forms), 0.01 to 0.5% by weight of 1,4-cyclohexanediol (both cis and trans forms), 0.01 to 1% by weight of formic acid, and numerous other mono- and dicarboxylic acids, esters, alcohols, aldehydes and so forth having individual contents of typically not exceeding 0.5% by weight. Examples of other mono- and dicarboxylic acids, esters, alcohols, aldehydes and other oxygen-containing compounds include acetic acid, propionic acid, butyric acid, valeric acid, caproic acid, oxalic acid, malonic acid, succinic acid, 4-hydroxybutyric acid and γ-butyrolactone.

Next, the aqueous layer containing the carboxylic acid mixture is concentrated. Concentration is normally carried out by distillation. As a result of distilling at a temperature of 10 to 250° C., preferably 20 to 200° C. and more preferably 30 to 200° C. and at a pressure of 0.1 to 150 KPa, preferably 2 to 110 KPa, and more preferably 10 to 105 KPa, the aqueous layer is concentrated by 1/50 to 1/2 times and preferably 1/20 to 1/3 times the amount prior to concentration. As a result of concentrating under these conditions, the water can be concentrated to 2% by weight or less and preferably 1% by weight or less of the total amount.

In this concentration, various carboxylic acids contained in the extracted aqueous layer are partially condensed to form oligomer esters.

Simultaneously with the treatment with an a lower alcohol of the carboxylic acid mixture (COA), which is obtained after extraction with water and concentration as above, to esterify the monocarboxylic acids and dicarboxylic acids contained in the concentrated extract, a step in which water, excess lower alcohol and carboxylic acid esters are removed and separated by distillation is carried out at the same time. These esterification and distillation and separation steps can be carried out in a single apparatus.

Examples of the lower alcohol used for esterification include methanol and ethanol, with methanol being used preferably.

In addition, the amount of the lower alcohol used is such that the mixing ratio (weight ratio) with respect to the aforementioned concentrated carboxylic acid mixture (COA) is 0.1 to 30, advantageously 0.5 to 15 and particularly advantageously 1 to 5.

During the esterification, the concentrated carboxylic acid mixture (COA) described above is dropped into the upper or intermediate portion of a reaction apparatus in a reaction vessel such as a stirring tank, bubble tower or distillation tower, a plurality of which may be used as necessary, and esterification is carried out by introducing the lower alcohol from the bottom of the reaction apparatus and allowing to react by co-flow, or by introducing a gas of the lower alcohol into a liquid phase of the aforementioned concentrated carboxylic acid mixture (COA), or by using a combination thereof. This reaction is normally carried out by heating, and a catalyst is used as necessary.

The lower alcohol can be introduced into the system as a liquid and then converted to a gas, or it can be introduced into the system after been gasified outside the system.

In the esterification comprised of introducing a lower alcohol into the liquid phase of the aforementioned concentrated carboxylic acid mixture (COA), the liquid phase can be stirred with a stirrer. In addition, a distillation column can be provided for the distillate gas to separate undesirable high boiling point components that have contaminated the esters.

Although the heating temperature can be suitably selected according to the type of lower alcohol used, the reaction can be carried out at a temperature of, for example, 50 to 400° C., preferably 100 to 300° C. and more preferably 150 to 250° C.

In addition, although the esterification step can be carried out under pressurized conditions, it can also be carried out at the pressure within the reaction apparatus used for the esterification reaction. Esterification is preferably carried out at a pressure of 0 to 5 MPa, more preferably 0.5 to 2 MPa and particularly preferably 1 to 1.5 MPa.

The reaction conditions regarding the aforementioned temperature and pressure can be suitably selected according to the type of lower alcohol used for esterification. In the case of using methanol, for example, a temperature of 100 to 300° C. (preferably 240° C.) and a pressure of 0.01 to 10 MPa (preferably 0.5 to 2 MPa) can be used.

Although the reaction time of the esterification step can be suitably selected according to the type of lower alcohol used, amount of the reaction compound and so forth, it can be made to be, for example, 0.3 to 10 hours and preferably 0.5 to 5 hours.

Although the esterification step can be carried out without adding a catalyst, it can also be carried out in the presence of a catalyst to increase the reaction rate. Homogeneously dissolving catalysts or solid catalysts can be used for the catalyst. Examples of homogeneously dissolving catalysts include mineral acids (such as sulfuric acid, phosphoric acid or hydrochloric acid), sulfonic acids (such as p-toluene sulfonic acid), heteropoly acids (such as phosphotungstenic acid), and Lewis acids (but only water-resistance and acid-resistant Lewis acids).

Acidic or hyperacidic materials can be used for the solid catalyst. The examples include acidic or hyperacidic metal oxides; $SiO_2$, $Al_2O_3$, $SnO_2$, $ZrO_2$, layered silicates or zeolite to which mineral acid group such as sulfate groups or phosphate groups have been added to increase acidity; and, ion exchange resins having sulfonic acid groups or carboxylic acid groups.

The solid catalyst can be used in the form of a fixed bed or a suspended bed.

In the case of a suspended bed, the amount of catalyst used is 0.1 to 5% by weight with respect to the total amount, and in the case of a fixed bed, the LHSV is within the range of 0.1 to 5 $h^{-1}$.

The amount used of homogeneously dissolving catalysts or solid catalysts is 0.01 to 1% by weight with respect to the total amount. Although the catalyst can be separated after the esterification step, it can also be used as a catalyst of the subsequent depolymerization step.

Figure 2:
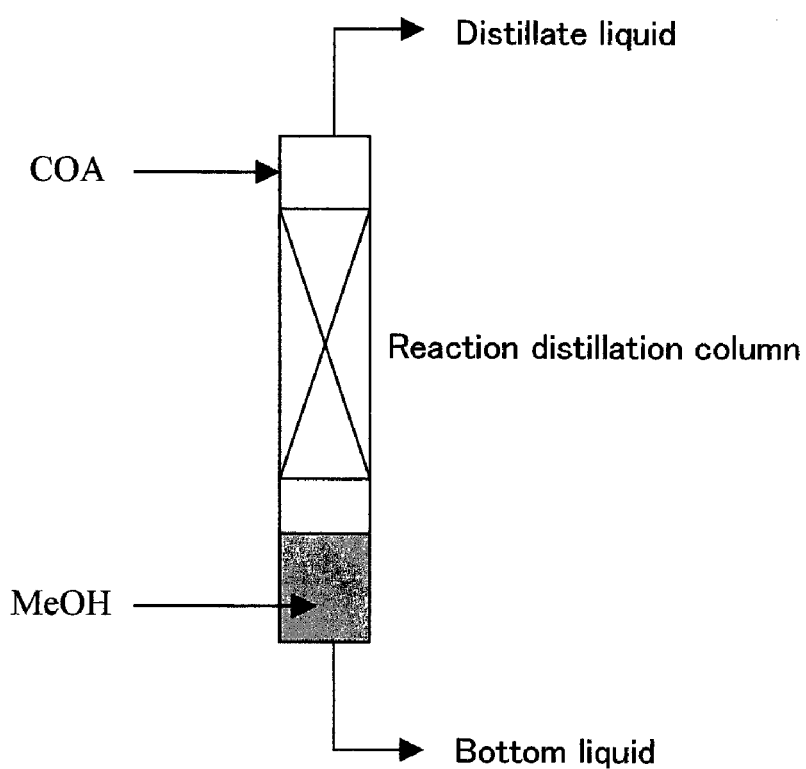
FIG. 2 shows an example of an esterification apparatus of the process of the present invention.

The following provides a more detailed explanation of the aforementioned esterification step. The esterification step can be carried out by, for example, a gas-liquid reaction in which a gaseous lower alcohol is introduced into a carboxylic acid mixture in a reaction apparatus (FIG. 1), or by a gas-liquid reaction in which a carboxylic acid mixture (COA) is dropped in from the upper or intermediate portion of a reaction distillation column such as a packed tower or tray tower and a gaseous lower alcohol is introduced from the bottom (FIG. 2). As a result of employing such a procedure, in addition to the esterification proceeding as a result of the alcohol dissolving in the liquid phase, the water formed in the liquid phase is released in the vapor phase, thereby allowing the water to be adequately removed from the system and being able to efficiently achieve a low acid value (AV) of 30 mgKOH/g or less.

In addition, the amounts of unreacted high boiling point components, such as adipic acid, 6-hydroxycaproic acid or 1,4-cyclohexanediol, in the carboxylic acid mixture, and a catalyst in the case of using a catalyst, mixed into the distillate are negligible and do not present a problem. Namely, the esterification step is characterized by the esterification reaction and distillation separation of undesirable substances being able to be carried out simultaneously.

The mixture of carboxylic acid esters, lower alcohol and water separated in the esterification step is introduced into a distillation column where the lower alcohol is distilled off at a pressure of 0.1 to 200 KPa and temperature of 0 to 150° C., and preferably a pressure of 10 to 150 KPa and temperature of 25 to 200° C. The resulting bottom liquid is either re-introduced into the distillation column or introduced into a second distillation column where the water is distilled off at a pressure of 0.1 to 150 KPa and temperature of 0 to 150° C., and preferably a pressure of 4 to 120 KPa and temperature of 25 to 120° C. The carboxylic acid esters separated from the aforementioned mixture in this manner can be further distilled prior to supplying to the subsequent hydrogenation step (3).

On the other hand, those compounds contained in the concentrated carboxylic acid mixture that have formed dimers with terminal hydroxyl groups of 6-hydroxycaproic acid and oligomer esters (referred to as oligomers) remain in the form of bottom liquid.

In step (2) of the present invention, oligomer esters contained in the bottom liquid after the water and carboxylic acid esters formed in step (1) and excess lower alcohol are distilled off, followed by distillative separation, are depolymerized at a high temperature and high pressure in the presence of a catalyst and lower alcohol to convert to carboxylic acid esters such as adipic acid ester and 6-hydroxycaproic acid ester.

Examples of catalysts that can be used in step (2) include homogeneously dissolving catalysts and solid catalysts. Although examples of homogeneously dissolving catalysts include mineral acids (such as sulfuric acid, phosphoric acid or hydrochloric acid), sulfonic acids (such as p-toluene sulfonic acid), heteropoly acids (such as phosphotungstenic acid), Lewis acids (such as aluminum compounds, vanadium compounds, titanium compounds, boron compounds or zinc compounds), and basic catalysts (such as oxides, carbonates, hydroxides, alcolates or amines of alkaline metals or alkaline earth metals), Lewis acids or basic catalysts are used preferably, while Lewis acids are used more preferably.

Examples of preferable Lewis acids include tetraalkoxytitanium, and more preferably tetra-n-butoxytitanium and tetraisopropoxytitanium.

In the process of the present invention, water formed by the esterification reaction and residual carboxylic acids are removed from the system in step (1), and deterioration of the aforementioned catalysts by acid and water is reduced in step (2), and therefore a Lewis acid can be used particularly preferably.

The amount of homogeneously dissolving catalyst used is typically 0.00001 to 0.01 and advantageously 0.0001 to 0.005 as the weight ratio with respect to the bottom liquid of step (1).

An acidic catalyst or hyperacidic catalyst can be used for the solid catalyst, examples of which include acidic or hyperacidic metal oxides; $SiO_2$, $Al_2O_3$, $SnO_2$, $ZrO_2$, layered silicates or zeolite to which mineral acid groups such as sulfate groups or phosphate groups and so forth have been added to increase acidity; and, ion exchange resins having sulfonic acid groups or carboxylic acid groups. The solid catalyst can be used in the form of a fixed bed or a suspended bed.

In the case of using a homogeneously dissolving acid catalyst for the catalyst, the reaction liquid may be neutralized with base following depolymerization. The amount of base used is 1 to 1.5 equivalents per acid equivalent of the catalyst. Typical examples of the base include oxides, carbonates, hydroxides, alcolates or amines of alkaline metals or alkaline earth metals. These can be used directly or they can be used after dissolving in the lower alcohol used for depolymerization.

Examples of lower alcohols that can be used in step (2) include methanol and ethanol, and methanol can be used preferably.

The amount of lower alcohol that can be used for depolymerization is 0.5 to 10 times (weight) and preferably 1 to 5 times the amount of distillation bottom liquid in step (1) containing oligomer esters.

The depolymerization reaction is carried out at a high temperature and high pressure, and more specifically, at a high temperature and a pressure higher than the vapor pressure curve of the depolymerization reaction liquid (liquid phase). More specifically, in the case of using methanol for the lower alcohol, the reaction is carried out in the liquid phase under conditions of 200° C. and 4 MPa or higher, preferably 240° C. and 8 MPa or higher, particularly preferably 250 to 280° C. and 9 to 15 MPa, and more preferably 265 to 275° C. and 9 to 12 MPa.

Figure 3:
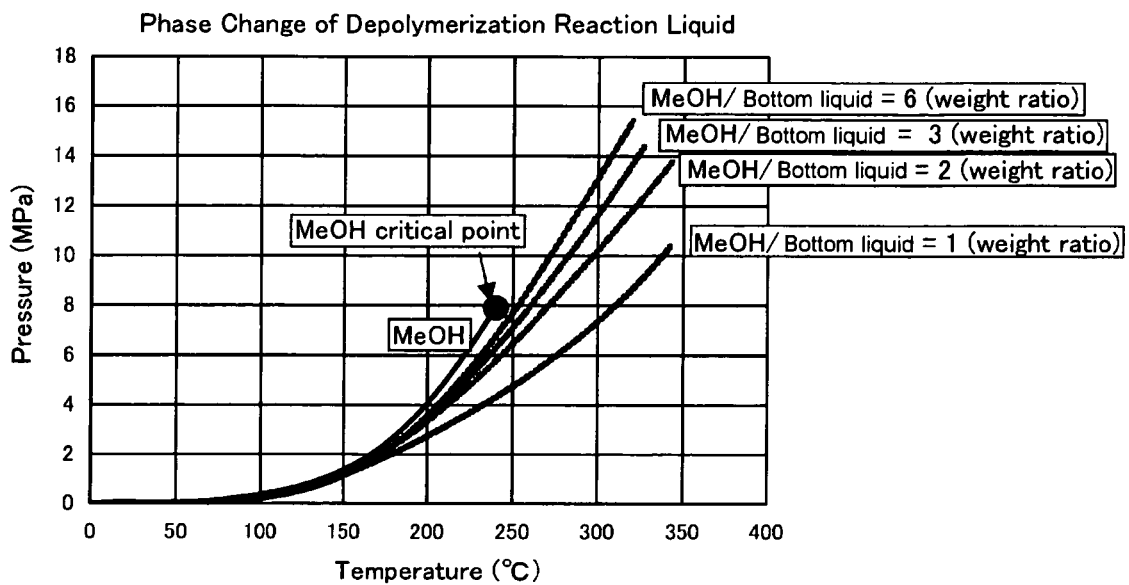
FIG. 3 is a phase change diagram of a depolymerization reaction of the process of the present invention.

An example of a vapor pressure curve indicating the phase change of the depolymerization reaction liquid in the case of changing the methanol/ester ratio using methanol for the lower alcohol is shown in FIG. 3.

Furthermore, this vapor pressure curve can be obtained by reducing the pressure in an autoclave equipped with an approximately 50 cc sapphire glass (visible apparatus), followed by charging ⅓ the volume of the bottom liquid after the esterification of step (1) and lower alcohol, and raising the temperature with the reaction vessel sealed while plotting the relationship between temperature and pressure. As a result of using conditions above this vapor pressure curve, namely using conditions such that the pressure is increased to a pressure above the vapor pressure curve (gas-liquid state), a uniform liquid phase results and the depolymerization reaction proceeds under these conditions.

Since the depolymerization reaction proceeds rapidly as a result of carrying out the depolymerization reaction in the liquid phase under the high temperature and high pressure as described above, the reaction time can be made to be 0.5 to 10 minutes and preferably 1 to 5 minutes. In addition, since the reaction is in a uniform phase, the scale of the reaction can be increased easily.

In specifically carrying out the depolymerization reaction, a lower alcohol and catalyst are added to the bottom liquid in step (1) followed by heating under pressure under the aforementioned conditions.

Since water formed by the esterification in the aforementioned step (1) is removed from the system and the acid value (AV) decreases, corrosion of the reaction vessel by acid and moisture is reduced.

Next, the excess lower alcohol used is removed by distillation from the reaction mixture after depolymerization. The pressure at that time is 0.1 to 150 KPa, preferably 2 to 100 KPa, and particularly preferably 4 to 80 KPa. The temperature at the top of the column is, for example, 0 to 150° C., preferably 15 to 90° C. and particularly preferably 25 to 75° C. The temperature at the bottom of the column is 70 to 250° C., advantageously 80 to 220° C. and particularly advantageously 100 to 200° C.

Furthermore, flash distillation, in which the pressure is released based on the depolymerization conditions, is preferably used for removal of excess lower alcohol.

As a result of distilling under these conditions, excess lower alcohol, water and low boiling point esters corresponding to, for example, formic acid, acetic acid and propionic acid, contained in the reaction mixture after depolymerization are separated. This matter flow can either be burned off or the recovered alcohol can be further reused in the esterification step or depolymerization step.

Separate from the aforementioned lower alcohol, water and low boiling point esters corresponding to, for example, formic acid, acetic acid and propionic acid, a mixture primarily containing carboxylic acid esters of the lower alcohol used and dicarboxylic acids such as adipic acid, glutaric acid and hydroxycarboxylic acids (such as 6-hydroxycaproic acid and 5-hydroxyvaleric acid), unreacted oligomer esters, free or esterified 1,4-cyclohexanediol and other high boiling point components is also separated.

This mixture is preferably applied to distillation prior to the hydrogenation of the subsequent step (3) to remove high boiling point components such as 1,4-cyclohexanediol and AV components that are poisonous to the hydrogenation catalyst (monocarboxylic acids and dicarboxylic acids contained in step (1) such as adipic acid, glutaric acid, 6-hydroxycaproic acid, 5-hydroxyvaleric acid and condensates thereof). This distillation may be carried out separately or in combination with distillation of the carboxylic acid esters separated by distillation together with water and alcohol following esterification in the previous step (1).

The pressure of this (ester) distillation step is 0.1 to 100 KPa, advantageously 0.1 to 10 KPa and particularly advantageously 0.3 to 5 KPa. The temperature at the top of the column is 50 to 200° C., advantageously 80 to 180° C. and particularly advantageously 90 to 150° C. The temperature at the bottom of the column is 70 to 250° C., advantageously 100 to 230° C. and particularly advantageously 130 to 220° C.

In addition, the bottom liquid obtained as a result of the aforementioned distillation can also be re-applied to depolymerization under the same conditions as described above to convert the oligomer esters contained in the bottom liquid to carboxylic acid esters. Since water is removed from the system in the aforementioned step (1), even in the case of having used a Lewis acid in the first round of depolymerization of step (2), since the Lewis acid is not subjected to deactivation by water, the Lewis acid may not again be added to this second depolymerization reaction. In this manner, the carboxylic acid esters obtained from the second round of depolymerization can be applied to the hydrogenation of the subsequent step (3) either separately or together with the previously obtained carboxylic acid ester to obtain 1,6-hexanediol.

In step (3) of the present invention, the carboxylic acid esters separated by distillation in the aforementioned step (1) and the carboxylic acid esters obtained in the aforementioned step (2) are hydrogenated followed by distillation to convert to 1,6-hexanediol.

The carboxylic acid esters separated by distillation in the aforementioned step (1) and the carboxylic acid esters depolymerized in the aforementioned step (2), and further applied to distillation depending on the case, can be hydrogenated separately or together. Hydrogenation reduction is carried out catalytically in the hydrogen gas phase or liquid phase using a catalyst.

All homogeneous or heterogeneous catalysts suitable for hydrogenation of carbonyl groups can be used for the hydrogenation catalyst, examples of which include metals, metal hydroxides, metal compounds and mixtures thereof.

Here, examples of homogeneous catalysts include those described in Houben-Weyl, Methoden der Organischen Chemie, Band IV/1c, GeorgThieme, Verlag Stuttgart, 1980.S.4567. In addition, examples of heterogeneous catalysts include those described in Houben-Weyl, Methoden der Organischen Chemie, Band IV/1c, S.16-26. Examples of metal catalysts that can be used include metals of subgroups I and VI to VIII of the periodic table described in the aforementioned non-patent document, and particularly copper, chromium, molybdenum, manganese, rhenium, ruthenium, cobalt, nickel and palladium, and one type or a plurality of types of these metals can be used.

Copper-containing hydrogenation catalysts can be used particularly preferably, specific examples of which include Cu—Cr, Cu—Zn, Cu—Zn—Al, Cu—Zn—Ti, Cu—Fe—Al and Cu—Si. In addition, there are no particularly limitations on the form of these catalysts, and may be suitably selected from forms such as a powder, granules or tablets according to the shape of the reaction vessel. In the case of a copper-zinc catalyst, a trace amount of aluminum, magnesium or zirconium and so forth may be contained.

A heterogeneous catalyst is used in the form of a fixed bed or suspended bed in the hydrogenation reaction.

Although the amount of catalyst can be suitably selected according to the type of catalyst, the LHSV is typically 0.1 to 5 $h^{-1}$ in the case of a fixed bed, while in the case of a suspended bed, the amount used can be 0.1 to 5% by weight with respect to the suspended bed.

In the case of carrying out the hydrogenation reaction in a gaseous phase, a fixed bed catalyst is used and the pressure is 0.1 to 15 MPa, preferably 0.5 to 12 MPa and more preferably 1 to 10 MPa.

The reaction temperature is 100 to 350° C. and preferably 120 to 300° C.

In the case of carrying out the hydrogenation reaction in the liquid phase, a fixed bed or a suspended bed can be used, and in either case the pressure is 1 to 35 MPa and the temperature is 100 to 350° C., and preferably 5 to 30 MPa and 200 to 300° C.

Hydrogenation reduction can be carried out in a single reaction vessel or can be carried out by connecting a plurality of reaction vessels in series. Although hydrogenation reduction can also be carried out discontinuously, it is preferably carried out continuously.

The reaction mixture obtained by carrying out hydrogenation reduction under the conditions described above primarily contains 1,6-hexanediol, while other components in the form of 1,5-pentanediol, 1,4-butanediol, 1,2-cyclohexanediol, small amounts of mono- or dialcohols having 1 to 7 carbon atoms and water are also obtained.

This reaction mixture can be separated by applying to a membrane system or distillation column into water and low boiling point components such as lower alcohols, and components primarily including 1,5-pentanediol, 1,2-cyclohexanediol and 1,6-hexanediol. The pressure during this distillation is 1 to 150 KPa, preferably 10 to 120 KPa and more preferably 20 to 110 KPa. The distillation temperatures are such that the temperature at the top of the column is 0 to 100° C. and preferably 30 to 70° C., while the temperature at the bottom of the column is 100 to 220° C. and preferably 120 to 200° C.

The component primarily containing 1,6-hexanediol obtained by the aforementioned distillative separation can be further purified in a distillation column to separate the 1,6-hexanediol from the 1,5-pentanediol, and 1,2-cyclohexanediol, and low boiling point compounds which may be present depending on the case. These distillation conditions can be adjusted to a pressure of, for example, 0.1 to 100 KPa, preferably 0.5 to 50 KPa and more preferably 1 to 10 KPa, a temperature at the top of the distillation column of, for example, 50 to 200° C. and preferably 60 to 200° C., and a temperature at the bottom of the distillation column of 130 to 250° C. and preferably 150 to 220° C. As a result of carrying distillative purification using a distillation column under such conditions, 1,6-hexanediol can be obtained at a purity of 99% or more.

In addition, in the case of desiring to acquire 1,5-pentanediol, this can be further separated with a distillation column.

EXAMPLE 1

The following provides a more detailed explanation of the present invention through examples thereof.

Step 1: Oxidation of Cyclohexane and Extraction with Water

Cyclohexane was oxidized under conditions of 160° C. and 1 MPa and then extracted using water under conditions of 160° C. and 1 MPa to obtain a carboxylic acid mixture having the composition indicated below.

Aqueous Extract of Cyclohexane Oxide
(Composition of Aqueous Extract)
Valeric acid: 0.1% by weight
5-hydroxyvaleric acid: 0.11% by weight
Caproic acid: 0.02% by weight
Succinic acid: 0.3% by weight
6-hydroxycaproic acid: 3.8% by weight
Glutaric acid: 0.3% by weight
Adipic acid: 2.7% by weight
1,2-cyclohexanediol: 0.02% by weight
1,4-cyclohexanediol: 0.04% by weight
Other: Water and trace components Step 2: Concentration of Aqueous Extract Next, the subject extract was concentrated under conditions of 13 KPa to obtain a concentrate having the composition indicated below.

Figure 4:
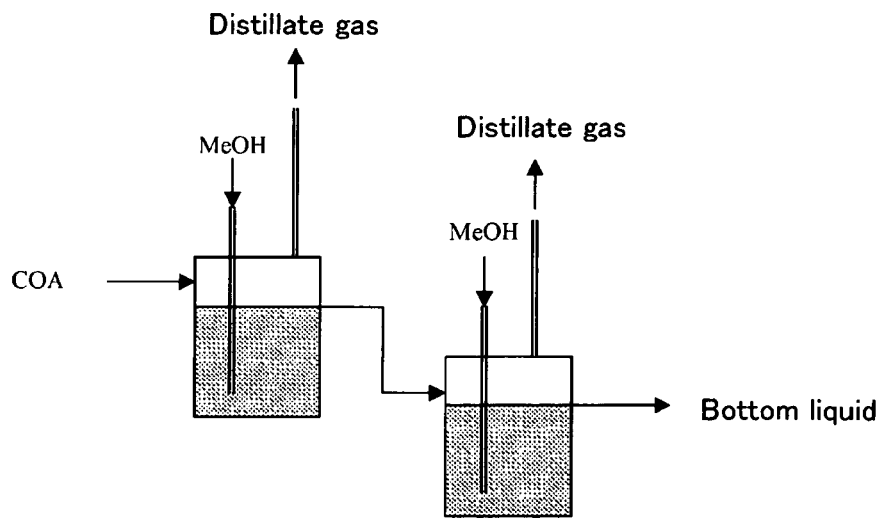
FIG. 4 is a drawing of an esterification apparatus of the process of the present invention.

(Composition)
Oxycaproic acid: 27.9% by weight (of which about 90% by weight was oligomers)
Adipic acid: 19.8% by weight (of which about 50% by weight was oligomers)
$H_2O$: 2.0% by weight
1,4-cyclohexanediol: 0.7% by weight Step 3: Esterification The bottom liquid (aforementioned concentrate) obtained in step 2 was continuously fed into a reaction apparatus (gas-liquid reaction tank, 700 cc×2 tanks, FIG. 4) at the rate of 700 g/h and the methanol was gasified followed by bubbling into the reaction liquid of the two tanks at 350 g/h, respectively. At that time, the temperature within the reaction tanks was maintained at 240° C. by external heating, and the pressure was adjusted with a back pressure regulating value so as to keep the distillate gas at 1 MPa. As a result, a distillate gas and bottom liquid were respectively obtained as indicated below.

Distillate Gas (after cooling and condensation): 757 g/h
$H_2O$: 6.9% by weight
Dimethyl adipate: 8.7% by weight
Methyl hydroxycaproate: 1.7% by weight
1,4-cyclohexanediol: Trace amount
Adipic acid: Trace amount
6-hydroxycaproic acid: Trace amount
Other: MeOH, low boiling point components Bottom Liquid: 643 g/h
Acid value (AV)=20 mgKOH/g
$H_2O$: 0.1% by weight
Other: Adipic acid, hydroxycaproic acid and other oligomer components Step 4: Recovery of Methanol and Distillative Removal of Water The distillate gas obtained as previously described was cooled and condensed followed by recovering the methanol with a first column according to the conditions indicated below and removing $H_2O$ and low boiling point components with a second column.

First Column:
Distillation apparatus: Sulzer Labo Packing EX (Sumitomo Heavy Industries), 5 units
Distillation conditions: 0.1 kg/cm$^2$G, column top: 66° C., column bottom: 111° C.

Second Column:
Distillation apparatus: Sulzer Labo Packing EX (Sumitomo Heavy Industries), 5 units
Distillation conditions: 410 Torr, column top: 76° C., column bottom: 190° C.

As a result, a concentrate was obtained having the composition indicated below.
MeOH: 0.2% by weight
Dimethyl adipate: 74.2% by weight
Methyl hydroxycaproate: 14.6% by weight
$H_2O$: 0.1% by weight
Caprolactone: 0.8% by weight
1,4-cyclohexanediol (cis+trans): ND
Dimethyl glutarate: 3.7% by weight
Dimethyl succinate: 1.2% by weight A study was made of comparative examples (esterification and concentrate in the absence of bubbling) with respect to the aforementioned example.

An esterification reaction was carried out by charging 6 kg of a carboxylic acid mixture (COA) and 3.9 kg of MeOH into a 20 L autoclave. The essentially reached equilibrium in 3 hours at 240° C. and 3 MPa, and the analytical values of the reaction liquid at that time consisted of an acid value (AV) of 42 mgKOH/g and an $H_2O$ content of 8.5% by weight.

This liquid was then concentrated using a 10 L evaporator at 30 to 250 Torr and oil bath temperature of 50 to 100° C. to obtain 5940 g of a concentrate having the composition indicated below.
MeOH: 0.2% by weight
Dimethyl adipate: 13.6% by weight (yield based on COA: 57%)
Methyl 6-hydroxycaproate: 16.0% by weight (yield based on COA: 55%)
$H_2O$: 0.1% by weight Step 5: Depolymerization The bottom liquid obtained in step 3 at 100 g/h, methanol at 200 g/h and tetrabutoxytitanium catalyst at 0.1 g/h were continuously fed into a tubular reactor followed by carrying out a depolymerization reaction under the conditions indicated below.

Reactor conditions: 270° C., 10 MPa, residence time: 5 minutes

The yield of dimethyl adipate and methyl 6-hydroxycaproate was 83%.

Step 6: Removal of Methanol

The reaction liquid obtained as a result of the depolymerization of step 5 was distilled under the conditions indicated below to remove the methanol and low boiling point fraction.

Distillation apparatus: Sulzer Labo Packing (5 units)
Distillation conditions: 160 Torr, column top: 34° C., column bottom: 89° C.

Step 7: Purification of Ester

The bottom liquid obtained in steps 4 and 6 was distilled under the conditions indicated below to obtain dimethyl adipate and methyl oxycaproate.

Distillation apparatus: Sulzer Labo Packing (27 units)
Distillation conditions: 5 Torr, column top: 70 to 111° C., column bottom: 117 to 188° C., reflux ratio: 10

Step 8: Hydrogenation

The esters obtained in step 7 underwent a hydrogenation reaction in a solid-liquid reaction tank under the conditions indicated below.

Hydrogenation apparatus: Suspended bed
Hydrogenation conditions: 250° C., 25 MPa, catalyst: CuO—ZnO catalyst (copper/zinc (metal weight ratio)=1/1): 1% by weight, 5 hours
Result: Saponification value conversion rate: 98%

Step 9: Purification of Diol 1000 g of the reaction liquid obtained in step 8 was purified by distillation under the conditions indicated below to obtain highly pure 1,6-hexanediol.

Distillation apparatus: Sulzer Labo Packing (30 units), reflux ratio: 10
Methanol main component: 257 g (760 Torr)
1,5-pentanediol main component: 60 g
1,6-hexanediol main component: 554 g (10 Torr, column top: 137 to 140° C., column bottom: 150 to 190° C.)

The composition of the impurities in the product fraction present in the 1,6-hexandiol main component was as indicated below.
1,4-cyclohexanediol: 0.1% by weight
1,2-cyclohexanediol: ND
1,5-hexanediol: ND
1,7-heptanediol: ND
1,5-pentanediol: 0.1% by weight Thus, the yield of 1,6-hexanediol was confirmed to be 90% or more, and additionally confirmed to be in excess of 95%.

Figure 5:
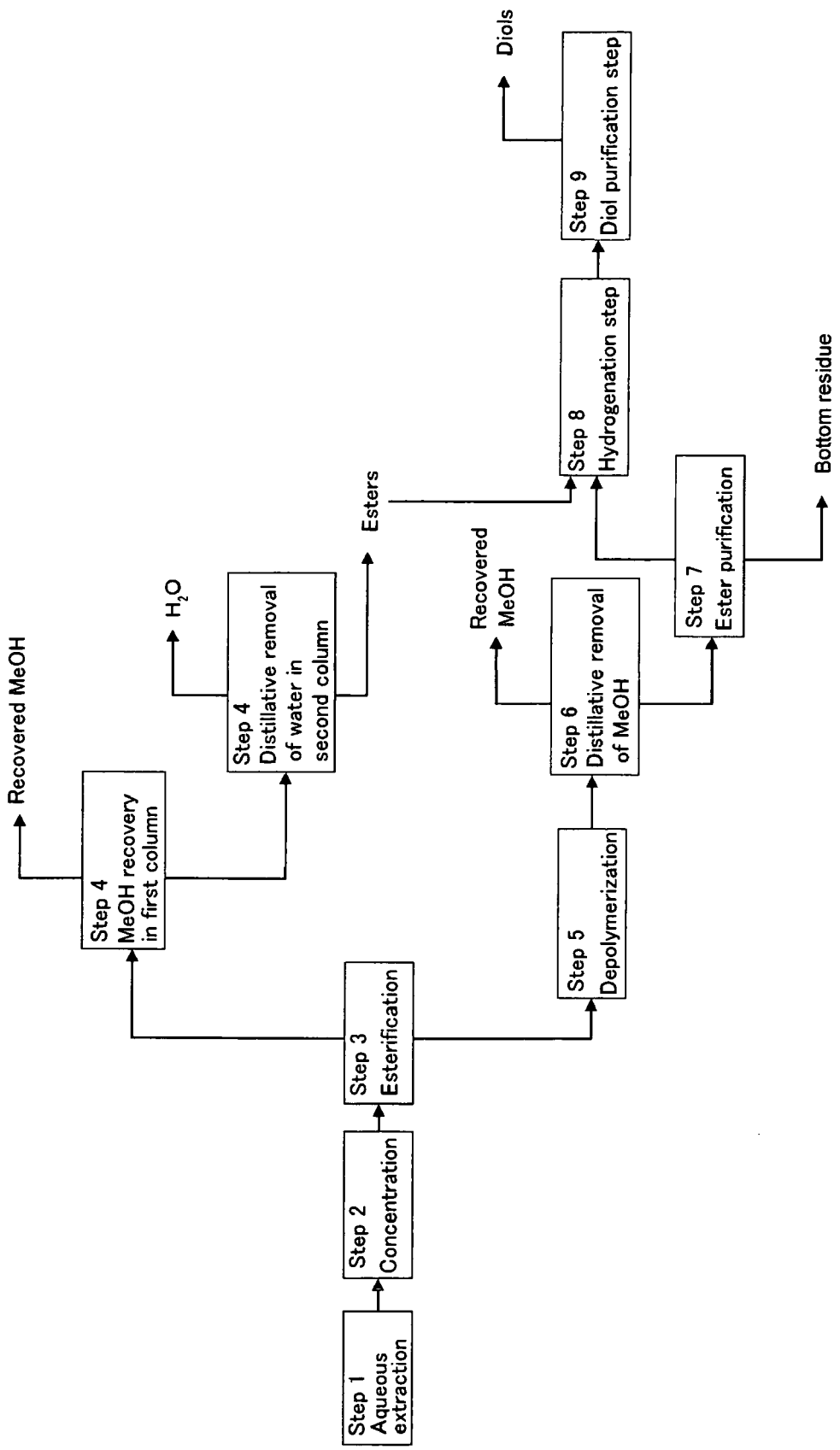
FIG. 5 is an example of a schematic flow chart of the process of the present invention; and,
FIG. 6 shows graphs indicating the effects of reaction temperature and reaction pressure on the yield of depolymerization in a depolymerization step.

A schematic drawing of the aforementioned steps 1 to 9 is shown in FIG. 5.

COMPARATIVE EXAMPLE 1

Example of Carrying Out Depolymerization Reaction without Separating Oligomers

A carboxylic acid mixture (concentrate of step 2: COA) at 100 g/h and methanol at 200 g/h were continuously fed to a tubular reactor under the conditions indicated below to obtain carboxylic acid esters.

Reactor conditions: 270° C., 10 MPa, residence time: 10 minutes

Reaction results: Yield of dimethyl adipate and methyl 6-hydroxycaproate: 35%

COMPARATIVE EXAMPLE 2

Example of Carrying Out Depolymerization Reaction without Separating Oligomers

A carboxylic acid mixture (concentrate of step 2: COA) at 100 g/h, methanol at 200 g/h and tetraisopropoxytitanium catalyst at 0.3 g/h were continuously fed to a tubular reactor under the conditions indicated below to obtain carboxylic acid esters.

Reactor conditions: 270° C., 10 MPa, residence time: 10 minutes

Reaction results: Yield of methyl adipate and methyl 6-hydroxycaproate: 40%

EXAMPLE 2

A study was made of the effect of water content on the acid value (AV) of the resulting bottom liquid (reaction liquid) and distillate gas by changing the amount of water in the methanol used in the esterification step of Step 3 in Example 1. The study was made under the conditions of a temperature of 200° C. or 240° C., pressure of 1.0 MPa, and 1:1 ratio of methanol to carboxylic acid mixture. The results are shown in Table 1. The acid values (AV) of both the bottom liquid and distillate gas tended to increase as the water content in the methanol increased.

TABLE 1

Effect of Water Content in MeOH (Two-tank gas-liquid stirring tank)

| Reaction tank | H$_2$O in MeOH wt % | Pressure MPa | MeOH/COA Weight ratio | Temperature ° C. | Liquid residence time h | Bottom liquid analytical values | | Distillate liquid analytical values | | | |
|---|---|---|---|---|---|---|---|---|---|---|---|
| | | | | | | AV mgKOH/g | H2O wt % | AV mgKOH/g | H2O wt % | DMA wt % | MOC wt % |
| 1st tank | 0.1 | 1 | 1 | 200 | 1.2 | 94 | 1.1 | 3.8 | 11.9 | 2.8 | 0.8 |
| 1st tank | 3.5 | 1 | 1 | 200 | 1.2 | 102 | 1.6 | 3.5 | 13.8 | 2.6 | 0.7 |
| 1st tank | 5 | 1 | 1 | 200 | 1.2 | 104 | 1.7 | 4.4 | 16 | 2.7 | 0.7 |
| 2nd tank | 0.1 | 1 | 1 | 240 | 0.7 | 23 | 0.1 | 2.9 | 3 | 7.6 | 2.8 |
| 2nd tank | 1 | 1 | 1 | 240 | 0.7 | 25 | 0.2 | 2.9 | 4 | 7.4 | 2.6 |
| 2nd tank | 3 | 1 | 1 | 240 | 0.7 | 33 | 0.4 | 3 | 5.5 | 7.3 | 2.5 |

Note:
Liquid in which the AV value had decreased to 100 mgKOH/g in the reaction of the first tank was fed to the second tank.

EXAMPLE 3

A study was made of the effects on the acid values (AV) of the resulting bottom liquid (reaction liquid) and distillate gas by changing the reaction type to an one-tank system (FIG. 1), a two-tank system (FIG. 4) and a reaction distillation system using a reaction distillation column (FIG. 2) in the esterification step of Step 3 in Example 1. The results are shown in Table 2. The best acid values were demonstrated to be obtained with a two-tank system.

TABLE 2

Effect of Reaction Type

| Reaction type | MeOH/COA | | | | Liquid phase residence time h | Bottom liquid analytical values | | Distillate liquid analytical values | | | |
|---|---|---|---|---|---|---|---|---|---|---|---|
| | Pressure MPa | Weight ratio | Temperature ° C. | | | AV mgKOH/g | H2O wt % | AV mgKOH/g | H2O wt % | DMA wt % | MOC wt % |
| One-tank type | 1.5 | 1 | 240 | | 2.2 | 45 | 1 | 6.1 | 14.2 | 4.9 | 1.6 |
| Two-tank type | 1.5 | 1 | 240 | | 1.4 | 17 | 0.4 | 2.5 | 4.6 | 6.5 | 2.3 |
| Reaction distillation | 1.5 | 1 | 240 | | 0.7 | 22 | 0.4 | 34 | 21 | 1.9 | 0.6 |

Note:
DMA: Dimethyl adipate,
MOC: Methyl 6-hydroxycaproate

EXAMPLE 4

A study was made of the effects on the acid values (AV) of the resulting bottom liquid (reaction liquid) and distillate liquid by changing the residence times in the first and second tanks in the esterification step of Step 3 in Example 1. The results are shown in Table 3.

TABLE 3

Effects of Residence Time (Two-tank gas-liquid stirring tank)

| Reaction type | MeOH/COA | | | Bottom liquid analytical values | | Distillate liquid analytical values | | | |
|---|---|---|---|---|---|---|---|---|---|
| | Pressure MPa | Weight ratio | Temperature °C. | Liquid residence time h | AV mgKOH/g | H2O wt % | AV mgKOH/g | H2O wt % | DMA wt % | MOC wt % |
| 1st tank | 11 | 1 | 200 | 0.7 | 112 | 1.2 | 4.9 | 11 | 2.5 | 0.7 |
| 1st tank | 11 | 1 | 200 | 1.2 | 94 | 1.1 | 3.8 | 11.9 | 2.8 | 0.8 |
| 1st tank | 11 | 1 | 200 | 2.2 | 79 | 1.1 | 4.4 | 11.8 | 3 | 0.8 |
| 2nd tank | 11 | 1 | 240 | 0.7 | 23 | 0.1 | 2.9 | 3 | 7.6 | 2.8 |
| 2nd tank | 11 | 1 | 240 | 2.2 | 11 | 0.2 | 1.5 | 3.3 | 8.4 | 3 |

Note:
Liquid in which the AV value had decreased to 100 mgKOH/g in the reaction of the first tank was fed to the second tank.

EXAMPLE 5

A study was made of the effects on the acid values (AV) of the resulting bottom liquid (reaction liquid) and distillate gas by changing the ratio of the methanol to the concentrated carboxylic acid mixture (COA) esterified in the esterification step of Step 3 in Example 1. The results are shown in Table 4.

TABLE 4

Effects of MeOH/COA Ratio (Two-tank gas-liquid stirring tank)

| Reaction type | MeOH/COA | | | Bottom liquid analytical values | | Distillate liquid analytical values | | | |
|---|---|---|---|---|---|---|---|---|---|
| | Pressure MPa | Weight ratio | Temperature °C. | Liquid residence time h | AV mgKOH/g | H2O wt % | AV mgKOH/g | H2O wt % | DMA wt % | MOC wt % |
| 1st tank | 1 | 0.5 | 200 | 1.2 | 110 | 2 | 5 | 20.2 | 2.5 | 0.5 |
| 1st tank | 1 | 1 | 200 | 1.2 | 94 | 1.1 | 3.8 | 11.9 | 2.8 | 0.8 |
| 1st tank | 1 | 2 | 200 | 1.2 | 87 | 0.6 | 3.6 | 6.7 | 2.6 | 0.8 |
| 2nd tank | 1.5 | 0.5 | 240 | 0.7 | 17 | 0.4 | 2.5 | 4.6 | 6.5 | 2.3 |
| 2nd tank | 1.5 | 1 | 240 | 0.7 | 12 | 0.2 | 1.3 | 2.9 | 6.2 | 2.6 |
| 2nd tank | 1.5 | 2 | 240 | 0.7 | 7 | 0.1 | 1 | 1.4 | 5.2 | 2.9 |

Note:
Liquid in which the AV value had decreased to 100 mgKOH/g in the reaction of the first tank was fed to the second tank.

EXAMPLE 6

A study was made of the effects on precipitation of tetrabutoxytitanium catalyst in the depolymerization reactor in the depolymerization step of Step 5 in Example 1 by changing the acid value (AV) of the bottom liquid (reaction liquid) in the esterification step of Step 3 in Example 1. There was demonstrated to be hardly any precipitation of tetrabutoxytitanium catalyst when the acid value (AV) in the bottom liquid (reaction liquid) was 30 mgKOH/g or less. The results are shown in Table 6.

EXAMPLE 7

A study was made of the effects on the acid values (AV) of the resulting bottom liquid (reaction liquid) and distillate liquid by changing the reaction pressure in the esterification step of Step 3 in Example 1. Those results are shown in Table 5.

TABLE 5

Effects of Pressure (Two-tank gas-liquid stirring tank)

| Reaction type | MeOH/COA | | | Bottom liquid analytical values | | Distillate liquid analytical values | | | |
|---|---|---|---|---|---|---|---|---|---|
| | Pressure MPa | Weight ratio | Temperature °C. | Liquid residence time h | AV mgKOH/g | H2O wt % | AV mgKOH/g | H2O wt % | DMA wt % | MOC wt % |
| 1st tank | 0.2 | 1 | 240 | 1 | 362 | 0.1 | 18 | 5.3 | 0.1 | 0.17 |
| 1st tank | 0.5 | 1 | 240 | 1 | 102 | 0.3 | 18 | 9.5 | 6 | 1.6 |
| 1st tank | 0.8 | 1 | 240 | 1 | 95 | 0.5 | 12 | 11 | 5.8 | 1.6 |
| 1st tank | 1 | 1 | 240 | 1 | 76 | 0.6 | 11 | 12.2 | 5.9 | 1.9 |
| 1st tank | 1.5 | 1 | 240 | 1 | 57 | 1 | 6.8 | 14 | 5.7 | 1.8 |
| 2nd tank | 0.2 | 1 | 240 | 0.7 | 90 | 0.1 | 5 | 2 | 1.2 | 0.4 |
| 2nd tank | 0.5 | 1 | 240 | 0.7 | 55 | 0.1 | 5 | 2.6 | 7 | 2.7 |

TABLE 5-continued

| | | Effects of Pressure (Two-tank gas-liquid stirring tank) | | | | | | | | |
|---|---|---|---|---|---|---|---|---|---|---|
| Reaction type | Pressure MPa | MeOH/COA Weight ratio | Temperature °C. | Liquid residence time h | Bottom liquid analytical values | | Distillate liquid analytical values | | | |
| | | | | | AV mgKOH/g | H2O wt % | AV mgKOH/g | H2O wt % | DMA wt % | MOC wt % |
| 2nd tank | 1 | 1 | 240 | 0.7 | 23 | 0.1 | 2.9 | 3 | 7.6 | 2.8 |
| 2nd tank | 1.5 | 1 | 240 | 0.7 | 12 | 0.2 | 1.3 | 2.9 | 6.2 | 2.6 |

Note:
Liquid in which the AV value had decreased to 100 mgKOH/g in the reaction of the first tank was fed to the second tank.

EXAMPLE 8

A study was made of the effects on yield by changing the amount of tetrabutoxytitanium catalyst used for the bottom liquid supplied for depolymerization in the depolymerization step of Step 5 in Example 1. The study was made under the conditions of using twice the amount of methanol (weight ratio), a temperature of 270° C. and a pressure of 11 MPa. The results are shown in Table 6. Yield tended to increase as the amount of catalyst increased.

EXAMPLE 9

Figure 6:
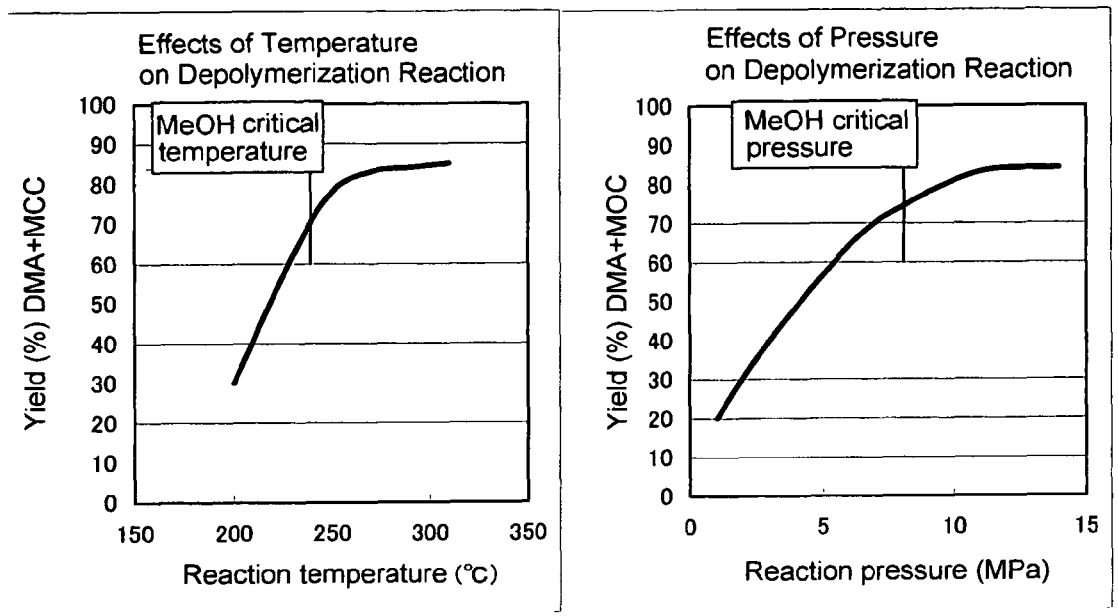

A study was made of the effects on depolymerization yield by changing the reaction temperature and reaction pressure in the depolymerization step of Step 5 in Example 1. The yield was demonstrated to be satisfactory at or above the critical temperature and critical pressure of methanol in the case of using methanol. The effects of reaction temperature and reaction pressure were studied under conditions of using 500 ppm of tetrabutoxytitanium and twice the amount of methanol (weight ratio) relative to the bottom liquid containing the oligomer supplied for depolymerization. The results are shown in Table 6 and FIG. 6.

EXAMPLE 10

A study was made of the effects on yield by changing the weight ratio of the methanol relative to the bottom liquid containing the oligomer supplied for depolymerization in the depolymerization step of Step 5 in Example 1. The study was made under the conditions of using 1000 ppm of tetrabutoxytitanium, a temperature of 270° C. and a pressure of 11 MPa. The results are shown in Table 6.

EXAMPLE 11

A study was made of the effects on yield by carrying out the depolymerization step of Step 5 in Example 1 under conditions of varying residence times and acid values (AV). The results are shown in Table 6.

TABLE 6

| | Depolymerization Reaction Results | | | | | | | |
|---|---|---|---|---|---|---|---|---|
| | Residence time min. | AV mgKOH/g | Temperature °C. | Pressure MPa | Methanol weight ratio | Catalyst concentration | Ti precipitation | Yield % |
| Effects of residence time | 0.5 | 30 | 270 | 11 | 2 | 1000 | Not observed | 48 |
| | 1 | 30 | 270 | 11 | 2 | 1000 | Not observed | 66 |
| | 3 | 30 | 270 | 11 | 2 | 1000 | Not observed | 82 |
| | 5 | 30 | 270 | 11 | 2 | 1000 | Not observed | 84 |
| | 10 | 30 | 270 | 11 | 2 | 1000 | Not observed | 85 |
| Effects of AV | 5 | 10 | 270 | 11 | 2 | 1000 | Not observed | 85 |
| | 5 | 30 | 270 | 11 | 2 | 1000 | Not observed | 84 |
| | 5 | 60 | 270 | 11 | 2 | 1000 | Observed | 80 |
| | 5 | 100 | 270 | 11 | 2 | 1000 | Observed | 75 |
| | 5 | 337 | 270 | 11 | 2 | 1000 | Observed | 31 |
| Effects of temperature | 5 | 30 | 230 | 11 | 2 | 500 | Not observed | 62 |
| | 5 | 30 | 250 | 11 | 2 | 500 | Not observed | 78 |
| | 5 | 30 | 270 | 11 | 2 | 500 | Not observed | 83 |
| | 5 | 30 | 290 | 11 | 2 | 500 | Not observed | 84 |
| Effects of pressure | 5 | 30 | 270 | 6 | 2 | 500 | Not observed | 66 |
| | 5 | 30 | 270 | 8 | 2 | 500 | Not observed | 70 |
| | 5 | 30 | 270 | 11 | 2 | 500 | Not observed | 83 |
| | 5 | 30 | 270 | 14 | 2 | 500 | Not observed | 84 |
| Effects of amount of methanol | 5 | 30 | 270 | 11 | 1 | 1000 | Not observed | 71 |
| | 5 | 30 | 270 | 11 | 2 | 1000 | Not observed | 84 |
| | 5 | 30 | 270 | 11 | 3 | 1000 | Not observed | 85 |
| | 5 | 30 | 270 | 11 | 6 | 1000 | Not observed | 86 |
| Effects of catalyst concentration | 5 | 30 | 270 | 11 | 2 | 0 | Not observed | 16 |
| | 5 | 30 | 270 | 11 | 2 | 100 | Not observed | 38 |
| | 5 | 30 | 270 | 11 | 2 | 500 | Not observed | 78 |
| | 5 | 30 | 270 | 11 | 2 | 1000 | Not observed | 84 |

Yield refers to the total yield of dimethyl adipate and methyl 6-hydroxycaproate.
Tetrabutoxytitanium was used for the catalyst.

[Industrial Applicability]

Use of the process of the present invention allows the obtaining of highly pure 1,6-hexanediol in which the contents of impurities that lower the polymerization rates during production of polyurethane and polyester, such as 1,4-cyclohexanediol, 1,5-hexanediol, 1,2-cyclohexanediol, 1,7-pentanediol, 1,5-pentanediol and high boiling point components, are significantly reduced. In addition, as a result of removing water and organic acids in the esterification step, Lewis acids and bases susceptible to water and organic acids can be used in the depolymerization step without being deactivated, while corrosion of the reactor can also be inhibited. Moreover, the rate of the depolymerization reaction can be significantly improved.

The invention claimed is:

1. A process for producing 1,6-hexanediol from cyclohexane, comprising the steps of:
   (1) treating an aqueous extraction concentrate of a reaction mixture obtained by oxidation of cyclohexane with a gaseous methanol or ethanol to esterify monocarboxylic acids and dicarboxylic acids contained in an extract in the form of a gas-liquid reaction, and simultaneously remove and separate by distillation, water, excess methanol or ethanol, and carboxylic acid esters;
   (2) converting oligomer esters contained in a bottom liquid to carboxylic acid esters by depolymerizing the oligomer esters at a temperature of 250 to 280° C. and at a pressure of 9 to 15 MPa in the presence of methanol or ethanol, and a catalyst; and
   (3) hydrogenating the carboxylic acid esters distilled off in the step (1) and the carboxylic acid esters obtained in the step (2) either respectively or collectively to convert to 1,6-hexanediol.

2. The process according to claim 1 wherein the esterification is carried out at 0 to 5 MPa in the step (1).

3. The process according to claim 1, wherein the depolymerization of the oligomer esters of step (2) is carried out using oligomer esters having an acid value of 30 mgKOH/g or less.

4. The process according to claim 1, wherein the depolymerization in the step (2) is carried out at a pressure higher than the vapor pressure curve of the oligomer esters.

5. The process according to claim 1, wherein the carboxylic acid esters obtained in the steps (1) and (2) are further supplied to distillation either separately or collectively.

6. The process according to claim 5, wherein the bottom liquid obtained following the distillation of the carboxylic acid esters is further depolymerized to convert to carboxylic acid esters followed by supplying to hydrogenation.

* * * * *